(12) United States Patent
Takesako et al.

(10) Patent No.: US 6,337,410 B2
(45) Date of Patent: Jan. 8, 2002

(54) ANTIBIOTIC TKR459, PRODUCTION METHOD, AND MICROORGANISM

(75) Inventors: Kazutoh Takesako, Otsu; Mitsuhiro Ueno; Naoyuki Awazu, both of Kusatsu; Kazuo Shimanaka, Takatsuki; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/731,041

(22) Filed: Dec. 7, 2000

Related U.S. Application Data

(63) Continuation-in-part of application No. 09/308,753, filed as application No. PCT/JP97/04271 on Nov. 25, 1997, now abandoned.

(30) Foreign Application Priority Data

Nov. 25, 1996 (JP) .............................. 8-330412

(51) Int. Cl.⁷ ........................ C07D 315/00; C12P 17/02
(52) U.S. Cl. ....................................... 549/417; 435/123
(58) Field of Search .......................................... 549/417

(56) References Cited

FOREIGN PATENT DOCUMENTS

| JP | 62-294676 | * 12/1987 |
| JP | 5-155877 | * 6/1993 |
| JP | 5-271215 | * 10/1993 |

* cited by examiner

*Primary Examiner*—Amelia Owens
(74) *Attorney, Agent, or Firm*—Connolly Bove Lodge & Hutz LLP.

(57) ABSTRACT

The present invention has its object to provide a noble antifungal substance which is use of as clinical medicine in the therapy of fungal infectious diseases.

The present invention is related to an antibiotic TKR459 having the following chemical formula (1) or its pharmacologically acceptable salt.

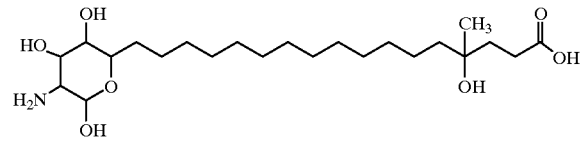

1 Claim, 5 Drawing Sheets

ANTIBIOTIC TKR459, PRODUCTION METHOD, AND MICROORGANISM

CROSS-REFERENCE TO RELATED APPLICATION

This application is a CIP of copending U.S. patent application Ser. No. 09/308,753 filed Jun. 22, 1999, which is the national phase of PCT/JP97/04271 filed Nov. 25, 1997.

TECHNICAL FIELD

The present invention relates to TKR459, which is an antibiotic of use as a therapeutic agent for fungal infectious diseases, a method for their production, and microorganisms producing said antibiotic.

BACKGROUND ART

Fungi are known to cause a variety of infectious diseases in man, animals, and plants. In man, for instance, they cause superficial mycosis affecting the skin, oral cavity, etc. and systemic mycosis affecting the viscera, brain, etc. They cause similar infections in pet and domestic animals as well. Furthermore, fungi inflict various hazardous effects on plants such as orchard trees and vegetables.

As the principal pathogenic fungi causing systemic mycosis in man, those of the genera Candida, Cryptococcus, and Aspergillus, among others, are known. As to superficial mycosis, Candida species affecting the skin, oral cavity, and vagina and Trichophytons infecting the skin of the extremities are regarded as the major pathogenic fungi. Besides those fungi, many other fungi exist in the environment and are suspected to contaminate the animal and vegetable kingdoms.

As antimycotics of use for the prevention and treatment of such fungal infections and contaminations, only a very few are known. Among them, as therapeutic drugs for systemic mycosis in man and animals, for instance, amphotericin B, flucytosine, miconazole, and fluconazole can be mentioned. However, those compounds are not fully satisfactory in potency, toxic potential, or antifungal spectrum, thus being not impeccable as therapeutic drugs.

SUMMARY OF THE INVENTION

In view of the above-mentioned prior art, the present invention has for its object to provide a novel antibiotic which is of value as a therapeutic agent for fungal infections.

In their search for a novel antibiotic, the inventors of the present invention isolated a large number of microorganisms from the natural kingdom, isolated the antibiotics they produced, and scrutinized their biological properties. As a result, they discovered that the culture broth of a strain of microorganism of the class Fungi Imperfecti contained an antibiotic having antifungal activity against pathogenic fungi inclusive of *Candida albicans, Candida kefyr*, and *Cryptococcus neoformans*. Accordingly the inventors isolated this antibiotic and studied its physicochemical properties. As a result, they discovered that the above antibiotic is a novel substance having distinct physicochemical characteristics and named it TKR459.

The present invention, therefore, is directed to the novel antibiotic TKR459 which is represented by the following chemical formula (1), or its pharmacologically acceptable salt.

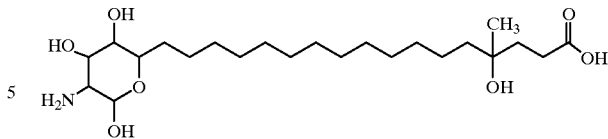

The present invention is further directed to a method of producing the antibiotic TKR459 which comprises culturing a strain of microorganism belonging to Fungi Imperfecti and capable of elaborating said antibiotic TKR459 and then isolating said substance from the resulting culture broth.

Furthermore, the present invention is directed to a microorganism belonging to Fungi Imperfecti and capable of producing the antibiotic TKR459.

DETAILED DESCRIPTION OF THE INVENTION

The present invention is now described in detail.

The antibiotic TKR459 of the present invention is represented by the chemical formula (1) described above.

The antibiotic TKR459 has the following physicochemical characteristics (1), (2), (3), (4), (5) and (6).

(1) Mass spectrum by FAB-MS gives a peak at m/z 448 $[M+H]^+$;

(2) The number of carbon atom is 23 and the number of nitrogen atom is 1;

(3) The specific optical rotation is $[\alpha]_D^{20}+8.1°$ (C 0.36, methanol);

(4) The UV spectrum in methanol has no characteristic absorptions;

(5) The wave numebers of major absorption in the IR spectrum by KBr method are 3400 $cm^{31\ 1}$, 2920 $cm^{-1}$, 2850 $cm^{-1}$, 1680 $cm^{-1}$, 1470 $cm^{-1}$, 1200 $cm^{-1}$, 1140 $cm^{-1}$, 840 $cm^{-1}$, 800 $cm^{-1}$, and 720 $cm^{-1}$.

(6) It is soluble in methanol and water, and sparingly soluble in hexane and chloroform.

Figure 3:
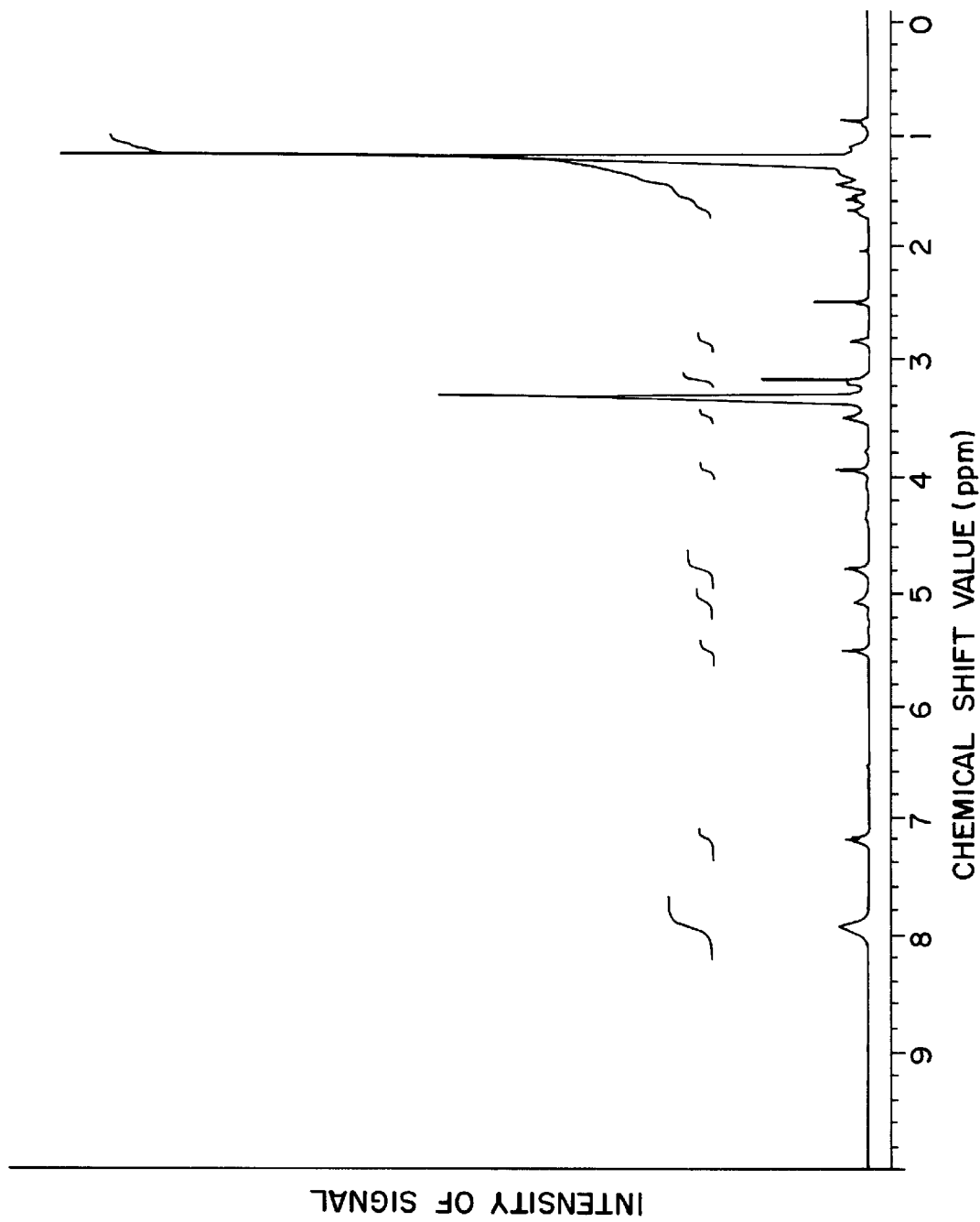
FIG. 3 is a chart showing the $^1$H-NMR spectrum of the antibiotic TKR459. The ordiante represents intensity of signal and the abscissa represents chemical shift value (ppm).
Figure 4:
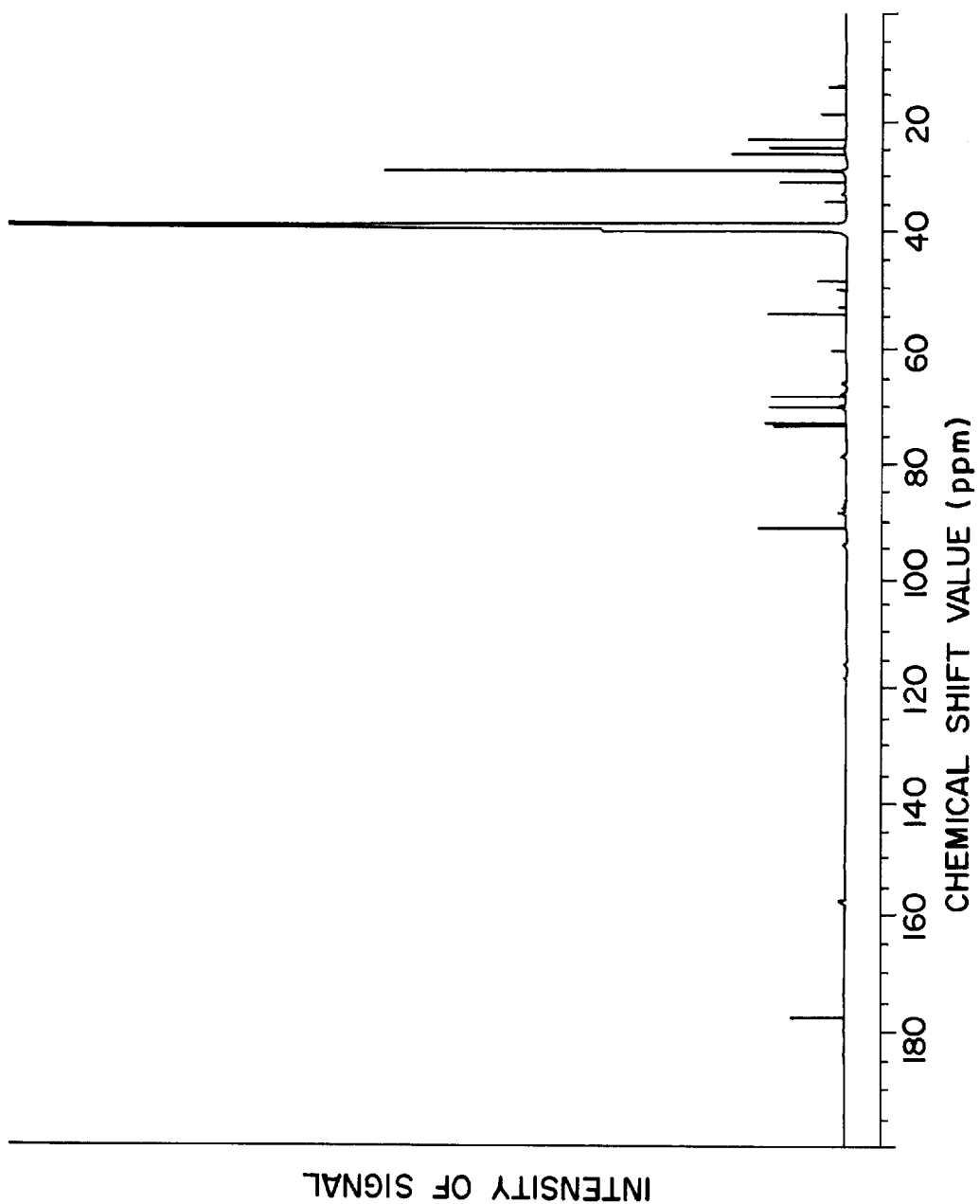
FIG. 4 is a chart showing the $^{13}$C-NMR spectrum of the antibiotic TKR459. The ordiante represents intensity of signal and the abscissa represents chemical shift value (ppm).
Figure 5:
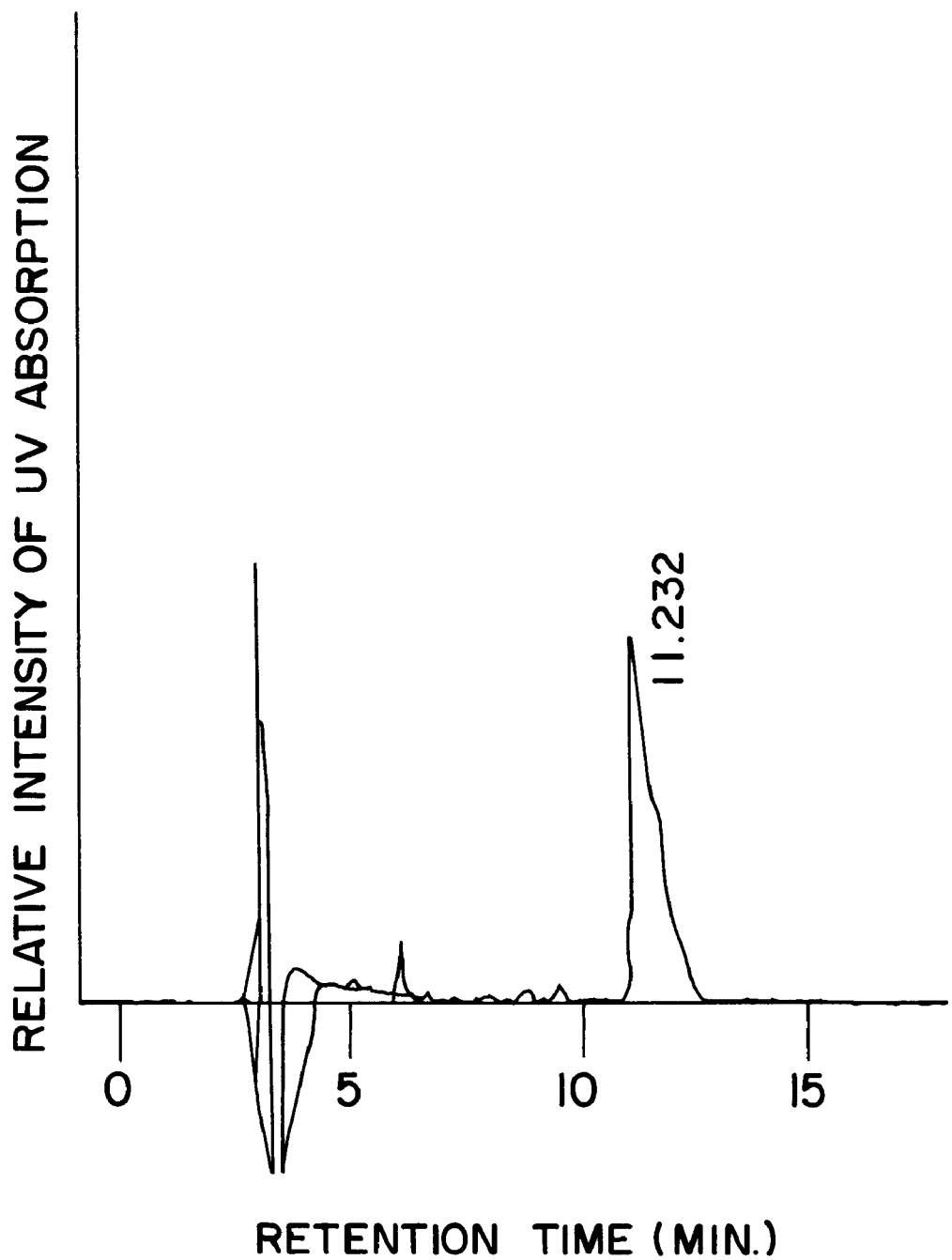
FIG. 5 is a HPLC chart of the antibiotic TKR459 showing its elution position. The ordinate represents the relative intensity of ultraviolet absorption and the abscissa represents retention time (min.).

Furthermore, TKR459 mentioned above is characterized in that it has the $^1$H-NMR spectrum shown in FIG. 3 and the $^{13}$C-NMR spectrum shown in FIG. 4, and in reversed-phase high-performance liquid chromatography, it is eluted at the position indicated in FIG. 5.

The above-mentioned TKR459 can be produced by growing a strain of microorganism belonging to the class Fungi Imperfecti and capable of producing said TKR459 and then isolating the substance from the resulting culture broth.

There is no limitation on the strain of microorganism that can be used in the present invention only provided it belongs to the class Fungi Imperfecti and is capable of producing said TKR459. Thus, for example, the fungi TKR459-strain belonging to the class Fungi Imperfecti (hereinafter referred to as the TKR459-strain) can be mentioned.

The above-mentioned TKR459-strain is a novel strain, and has never described in literatures, and isolated and characterized for the first time by the inventors of the present invention. The strain has the property to produce TKR459 with advantage. The mycological characteristics of this TKR459-strain are now described in detail.

The colonial colors of said TKR459-strain on various media are shown in Table 1. The descriptions of colors in the table are based on those prescribed in Japanese Industrial Standard (JIS) Z 8102 (1985) and reflect the results of observation on day 14 of culture at 25° C. after inoculation in the respective media.

TABLE 1

| Medium | Colony size diameter (mm) | Color or colony | Reverse color of the colony | Texture of the colony |
| --- | --- | --- | --- | --- |
| Malt extract agar | 13 | Dark grayish yellow red 10R4/3 | Dark brown 2.5YR3/2 | Ropy |
| Potato dextrose agar | 17 | Dark grayish yellow red 10R4/3 | rusty 2.5YR3/4 | Ropy |
| Sabouraud agar | 19 | Darkish yellow 2.5GY8/4 | Darkish yellow 2.5Y8/6 | Velvety |
| YpSs agar | 23 | Light yellow 2.5Y9/4 | Light yellow 2.5Y9/4 | Velvety |

The above TKR459-strain grows slowly on malt extract agar, potato dextrose agar, and Sabouraud agar etc., giving colonies showing a ropy or velvety surface texture and a elevated center with dense hard mycelia. The conidia of the TKR459-strain are unicellar, have a shape like cylinder or cask whose both sides are round and surface is smooth, and measure 4 to 6×1.5 to 2.5 $\mu$m. Lots of conidia are formed or the above media, but the conidia formation style from the conidiophore was unidentified.

Among the mycological characters of the TKR459-strain, its physiological characteristics are as follows.

Temperature range for growth: The temperature range for growth is 10 to 30° C. and the optimum range of temperature for growth is about 25°C.

The pH range for growth: The pH range for growth is pH 3 to 8 and the optimum range of pH for growth is about pH 4 to 7.

When the above mycological characters are compared with the descriptions of the genera of Fungi Imperfecti in Joseph c. Gilman, A Manual of Soil Fungi. Constable and Company Ltd., 1959, and other literatures, the genus of TKR459-strain can not be identified because of unidentification of the conidia formation style.

However, no report was available on a strain of microorganism having the ability to produce TKR459 among fungi of the class Fungi Imperfecti. Therefore, the inventors of the present invention regarded it as a novel strain and named fungi TKR459belonging to Fungi Imperfecti. The strain was deposited at National Institute of Bioscience and Human Technology, Agency of Industrial Science and Technology (Address, 1–3, Higashi 1-chome, Tsukuba-shi, Ibaraki, Japan (Zip code 305)) under the accession number of FERM BP-6094 (original date of deposit: Oct. 8, 1996; date of request for transfer to international deposit: Sept. 2, 1997).

The present invention can be carried into practice not only with the above-mentioned TKR459-strain but also with any spontaneous or artificial mutant of said TKR459-strain or any other strain of microorganism belonging to the class Fungi Imperfecti and capable of producing TKR459.

In accordance with the present invention, TKR459 is produced by seeding and cultivating a TKR459-producing strain in a nutrient medium. As said nutrients, carbon sources include glucose, fructose, saccharose, starch, dextrin, glycerol, molasses, malt syrup, oils and fats, and organic acids.

Nitrogen sources as nutrients include organic and inorganic nitrogenous substances such as soybean meal, cotton seed meal, corn steep liquor, casein, peptone, yeast extract, meat extract, wheat germs, urea, amino acids, ammonium salts, etc. Salts as nutrients are various inorganic salts such as salts of sodium, potassium, calcium, magnesium, etc. and salts of phosphoric acid. Those substances can be used independently or in a suitable combination.

Where necessary, the nutrient medium may be supplemented with heavy metal salts such as iron salts, copper salts, zinc salts, cobalt salts, etc., vitamins such as biotin, vitamin $B_1$, etc., and other organic and inorganic substances which would assist in growth of the microorganism and promote production of TKR459.

In addition to the above components, an antifoamer and/or a surfactant, for example silicone oil, polyalkylene glycol ethers, etc., can be added to the nutrient medium.

In cultivating a strain of microorganism capable of producing TKR459 in said nutrient medium, a variety of cultural methods which are generally used in the production of antibiotics by culture of microorganisms can be employed. However, liquid culture, particularly shake culture or submerged aerobic culture, is preferred.

The cultivation is preferably carried out at 15 to 25° C. The pH of the medium may range from pH 3 to 8 but is preferably around pH 5. Regarding the incubation time, generally a sufficient output of the antibiotic can be expected by 6 to 11 days of culture.

By the above cultivation, TKR459 is contained both intracellularly and extracellularly and accumulated in the culture broth. In the present invention, the TKR459 accumulated in the culture broth can be recovered and isolated from the broth by utilizing its physicochemical characteristics and, where necessary, by further purification.

The above-mentioned isolation can be achieved by extracting the whole broth with a non-hydrophilic organic solvent such as ethyl acetate, butyl acetate, chloroform, butanol, methyl isobutyl ketone, or the like. As an alternative, it is possible to subject the broth to centrifugation or filtration to separate into the medium and cells and isolate the antibiotics from each of the medium and cells.

TKR459 can be separated from the medium not only by the above-mentioned extraction method using a non-hydrophilic organic solvent but also by the method which comprises contacting the medium with an adsorbent to let TKR459 adsorbed on the adsorbent and desorbing or eluting them with a solvent. The adsorbent that can be used includes, for example, activated carbon, cellulose powder, and adsorbent resins. As the above-mentioned solvent, a variety of solvents can be selectively used according to the kind and properties of the adsorbent and either singly or in combination. Thus, an aqueous solution of one or more water-soluble organic solvents, such as aqueous acetone, aqueous alcohol, etc., can be employed. For isolation of TKR459 from the microorganisms, the extraction technique using a hydrophilic organic solvent such as acetone can be employed.

In the present invention, the crude extract of TKR459 from the culture broth can further be purified. The purification can be carried out by the conventional techniques for the isolation and purification of hydrophobic antibiotics, for example, by column chromatography or high-performance liquid chromatography, using an absorbent such as silica gel, activated alumina, activated carbon, adsorbent resin, etc. In case of using silica gel column chromatography, the eluent includes chloroform, ethyl acetate, methanol, acetone, water, etc. and these can be used in combination of two or more than two kinds.

In case of using high-performance liquid chromatography, adsorbents include chemically-derivatized silica gel, such as silica gel derivatives having octadecyl, octyl, or phenyl groups, and polystyrenic porous polymer gels, while the mobile phase that can be used includes aqueous solutions of water-soluble organic solvents, such as aqueous methanol, aqueous acetonitrile, etc.

TKR459 can each be put to use as such or in the form of a pharmacologically acceptable salt in medicinal applications. There is no particular limitation on the type of pharmacologically acceptable salt. Thus, the salt includes salts of mineral acids such as hydrochloric acid, sulfuric acid, nitric acid, phosphoric acid, hydrofluoric acid, hydrobromic acid, etc., salts of organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc., and salts of alkali metals or alkaline earth metals, such as sodium, potassium, calcium, etc.

When administering TKR459 or its pharmacologically acceptable salt of the present invention, as a pharmaceutical, they can be administered to animals inclusive of humans either as such or in the form of a pharmaceutical composition containing typically 0.1 to 99.5%, preferably 0.5 to 90% thereof in a pharmaceutically acceptable, non toxic and inert carrier.

The carrier mentioned above includes solid, semisolid or liquid diluents, fillers, other formulation auxiliaries, etc. and such carriers can be used alone or in combination.

The above-mentioned pharmaceutical composition is preferably administered in unit dosage forms and can be administered orally, parenterally, topically (e.g. transdermally) or rectally. Of course, those pharmaceutical compositions should be administered in dosage forms suited for the respective route of administration.

For administration of TKR459, or its pharmacologically acceptable salt, as a drug, the dose as an antifungal agent is preferably selected with reference to patient factors such as age and body weight, route of administration, nature and severity of disease, etc. Usually in man, however, the daily dose of the active ingredient for an adult patient is 10 to 2000 mg. While a daily dose lower than the above range may be sufficient in some cases, a dose higher than the range may be required in other cases. When a high dose is used, the daily dosage is preferably administered in several divided doses.

The oral administration can be made using solid, powdery, or liquid dosage forms such as powders, dilluted powders, tablets, dragees, capsules, drops, sublingual tablets, etc.

For the parenteral administration, liquid unit dosage forms for subcutaneous, intramuscular, or intravenous administration, of typically solutions and suspensions, can be employed. These preparations can be manufactured by suspending or dissolving a predetermined amount of TKR459, or a pharmaceutically acceptable salt thereof of the present invention, in a nontoxic liquid carrier suitable for injection, such as an aqueous medium or an oily medium, and sterilizing the resulting suspension or solution.

The topical administration (e.g. transdermal administration) can be carried out using a variety of topical dosage forms such as liquids, creams, powders, pastes, gels, and ointments. These dosage forms can be manufactured by using a predetermined amount of TKR459 or a pharmacologically acceptable salt thereof of the present invention, in combination with one or more of the perfume, coloring agent, filler, surfactant, humectant, emollient, gelatinizer, carrier, preservative, stabilizer, etc., suitable for topical dosage formulations.

The rectal administration can be made using, for example, suppositories each mixing a predetermined amount of TKR459, or its pharmacologically acceptable salt of the present invention, with a low-melting solid base such as higher esters, e.g. myristyl palmitate, polyethylene glycol, cacao butter, or a mixture of them.

BEST MODE OF CARRYING OUT THE INVENTION

The following examples are further illustrative of the present invention, but by no means limitative of the scope of the invention.

EXAMPLE 1

A loopful of TKR459-strain (FERM BP-6094) from a slant culture was used to inoculate into a 500-ml Erlenmeyer flask containing 100 ml of liquid medium (Difco yeast nitrogen base 0.67% (w/v), glucose 2.0% (w/v)) and incubated on a shaker at 25° C. for 3 days to prepare a seed culture. This seed culture 1.0 ml was transferred to 20 Erlenmeyer flasks of 500 ml capacity each containing 120 ml of the same liquid medium as above and incubated (under shaking at 220 rpm) at 25° C. for 8 days. The obtained culture broth was centrifuged and the supernatant was separated from cells. Methanol (1 L) was added to the cells, the mixture was sufficiently mixed, and the extract was concentrated under reduced pressure. Water and butanol (each 300 ml) were added to the resulting residue, and the mixture was sufficiently mixed and extracted with butanol. The extract was concentrated under reduced pressure and gave a residue (1016 mg). The residue was treated with a extraction with liquid-liquid partition using n-hexane/acetonitril/trifluoroacetic acid (100:100:0.5). The lower layer was concentrated, and extracted with methanol to yield a crude extract (207 mg). The extract was dissolved in a small volume of methanol and subjected to high-performance liquid chromatography to provide an active fraction. The fraction was concentrated under reduced pressure and gave a resiue (83.7 mg). The high-performance liquid chromatography was carried out under the following conditions.

Apparatus: LC6B (manufactured by Shimadzu) Column: YMC pack C18 (2.0 cm×25 cm) (manufactured by YMC).

Mobile phase: 25 to 100% (v/v) of methanol containing 0.05% trifluoroacetic acid.

The residue was dissolved in 0.4 ml of methanol and subjected to high-performance liquid chromatography to give an active fraction. This fraction was concentrated under reduced pressure to provide 9.3 mg of pure TKR459 as white powder. This high-performance liquid chromatography was carried out under the following conditions.

Apparatus: LC8A (manufactured by Shimadzu).

Column: YMC pack C18 (2.0 cm×25 cm) (manufactured by YMC).

Mobile phase: 0.05% trifluoroacetic acid-containing 45% (v/v) acetonitrile/water.

Physicochemical Properties

Mass spectrometry was carried out by JMS-DX302 mass spectrometer (manufactured by Jeol Ltd.). $^1$H-NMR (in deuterated dimethyl sulfoxide with dimethyl sulfoxide as reference) and $^{13}$C-NMR (in deuterated dimethyl sulfoxide with deuterated dimethyl sulfoxide as reference) were performed by JNM-A500 nuclear magnetic resonance spectrometer (manufactured by Jeol Ltd.). Specific optical rotation (in methanol) was determined by DIP370 digital polarimeter (manufactured by Jasco Ltd.). Ultraviolet spectrophotometry (in methanol) was carried out by UV-250 self-recording spectrophotometer (manufactured by Shimadzu), and infrared absorption spectrometry (KBr method) was by 270-30 infrared spectrophotometer (manufactured by Hitachi). Physicochemical properties of the substance TKR459 were described below.

(1) Mass spectrometry

The purified white powdery product obtained by concentration of the active fraction in said high-performance liquid chromatography under reduced pressure was found by FAB-MS to be a substance with a peak at m/z 448 [M+H]$^+$.

(2) Number of carbon and nitrogen atoms

The purified white powdery product obtained by concentration of the active fraction in said high-performance liquid chromatography under reduced pressure was found to be 23 carbon atoms and one nitrogen atom by $^1$H-NMR spectrum, $^{13}$C-NMR spectrum, and their anlyses.

The $^1$H-NMR spectrum and $^{13}$C-NMR spectrum of this product are presented in FIG. 3 and FIG. 4, respectively.

(3) Specific optical rotation

The specific optical rotation in methanol of the purified white powdery product obtained by concentration of the active fraction in said high-performance liquid chromatography under reduced pressure was found to be $[\alpha]_D^{20}$+8.1° (C 0.36, methanol)

(4) Ultraviolet absorption spectrum

The UV absorption in methanol of the purified white powdery product obtained by concentration of the active fraction in said high-performance liquid chromatography under reduced pressure was found to be no characteritic absorption.

Figure 1:
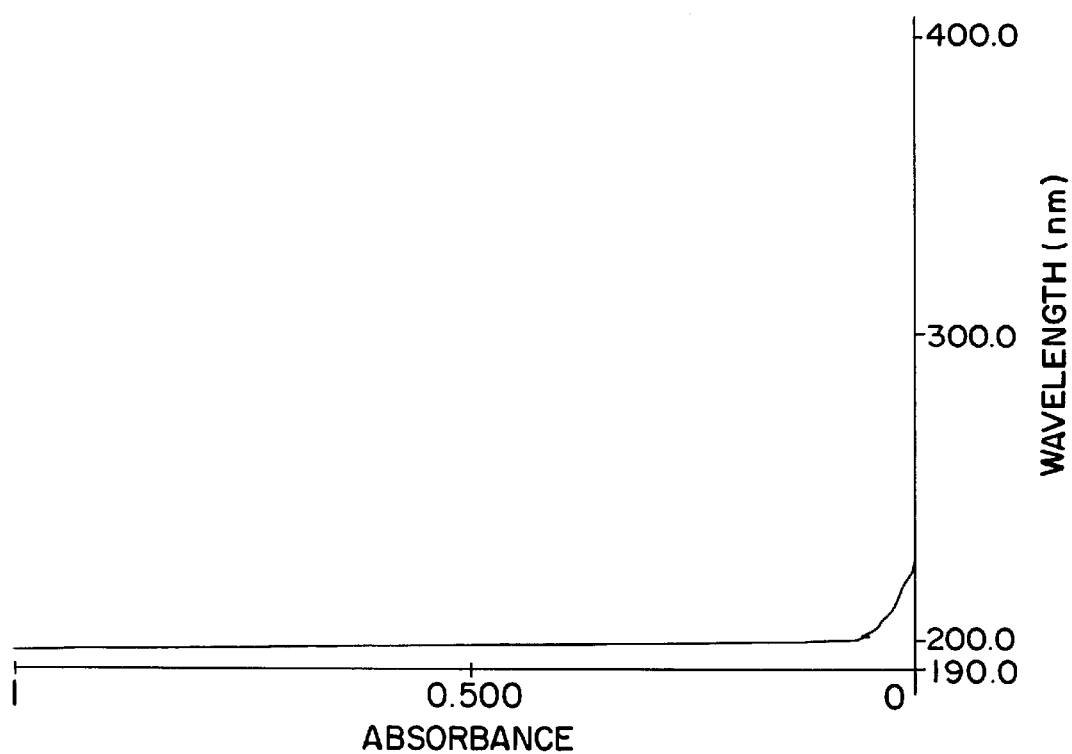
FIG. 1 is a chart showing the ultraviolet absorption spectrum of the antibiotic TKR459. The ordinate represents wave length (nm) and the abscissa represents absorbance.

The UV absorption spectrum is shown in FIG. 1.

(5) Infrared absorption spectrum

The IR spectrophotometric characterization (KBr method) of the purified white powdery product obtained by concentration of the active fraction in said high-performance liquid chromatography under reduced pressure revealed the following numbers of wave length of major absorption.

IR (KBr) (cm$^{-1}$): 3400, 2920, 2850, 1680, 1470, 1200, 1140, 840, 800, 720.

Figure 2:
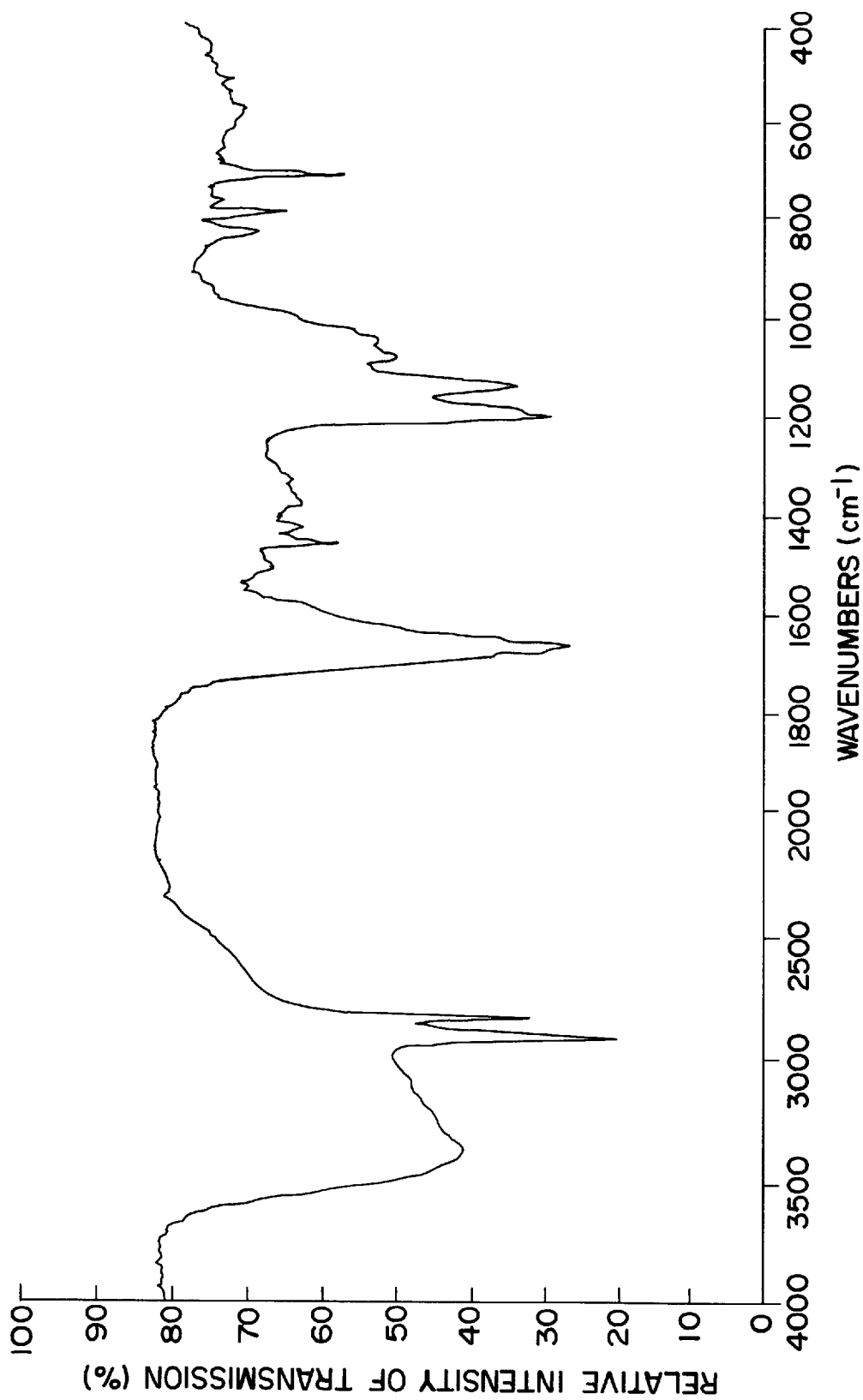
FIG. 2 is a chart showing the infrared absorption spectrum of the antibiotic TKR459. The ordinate represents relative intensity of transmission (%) and the abscissa represents wave numbers ($cm^{-1}$).

The IR absorption spectrum is shown in FIG. 2.

The above powder was soluble in methanol and water, but sparingly soluble in chloroform and hexane.

Based on the above analyses, the purified white powdery product obtained by concentration of the active fraction in said high-performance liquid chromatography under reduced pressure was identified to be TKR459.

The above TKR459 was analyzed by reversed-phase partition high-performance liquid chromatography (HPLC) using LC-10A high-performance liquid chromatography (manufactured by Shimadzu). This HPLC analysis was carried out under the following conditions.

Column: CAPCELLPAK C$_{18}$ (6 mm×150 mm) (manufactured by Shiseido).

Mobile phase: 0.05% trifluoroacetic acid-containing 40% (v/v) acetonitrile/water.

Column temperature: 40° C.

Detection UV wave length: 220 nm.

As a result, the above TKR459 was found to be eluted in the position indicated in FIG. 5.

Biological characteristics

The TKR459 obtained was used to determine antimicrobial spectra against various microorganisms. The minimal inhibitory concentration (µg/ml) was measured by the liquid medium dilution method as the minimal concentration causing a substantially complete inhibition of micobial growth. The results are presented in Table 2. The sub-minimal inhibitory concentration (µg/ml) was determined as the minimal concentration causing a partial inhibition of micobial growth and shown in the parentheses of Table 2. In the table, YNBG stands for a medium comprising 0.67% of yeast nitrogen base (manufactured by Difco) and 1.0% of glucose.

TABLE 2

| Test strain | Medium | Minimal inhibitory concentration (µg/ml) |
|---|---|---|
| Candida albicans TIMM0136 | YNBG | 0.78 |
| Candida kefyr TIMM0301 | YNBG | 0.78 (0.39) |
| Cryptococcus neoformans TIMM0354 | YNBG | 3.13 |

It is apparent from Table 2 that TKR459, the antifungal substance according to the present invention, was active against pathogenic fungi such as *Candida albicans, Candida kefyr, Cryptococcus neoformans* etc.

Intraperitoneal administration of the TKR459 obtained above at the dose of 100 mg/kg to ICR mice caused no toxic signs.

INDUSTRIAL APPLICABILITY

As described above, the present invention provides the antifungal substance tkr459 which is of use as clinical medicine, for example in the therapy of fungal infectious diseases, and a method for production of the substance.

What is claimed is:

1. TKR459, an antibiotic having the following chemical formula (1) or its pharmacologically acceptable salt.

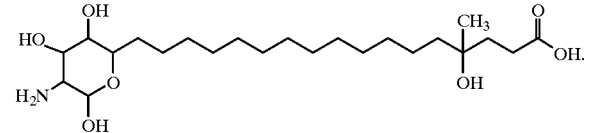

* * * * *